United States Patent [19]
Wolk et al.

[11] Patent Number: 5,579,786
[45] Date of Patent: Dec. 3, 1996

[54] AUTOMATIC DENTAL FLOSSING DEVICE

[76] Inventors: Roger S. Wolk, 28 Malibu Colony Dr., Malibu, Calif. 90265; Claudette Tapocik, 4105 Indus Way, Riverside, Calif. 92503

[21] Appl. No.: 387,486

[22] Filed: Feb. 13, 1995

[51] Int. Cl.[6] .................................................. A61C 15/00
[52] U.S. Cl. .......................................... 132/322; 433/118
[58] Field of Search ............................ 433/118; 132/322, 132/323

[56] References Cited

U.S. PATENT DOCUMENTS

| | | |
|---|---|---|
| 4,235,253 | 11/1980 | Moore . |
| 4,245,658 | 1/1981 | Lecouturier . |
| 4,509,541 | 4/1985 | Manciocchila ........................ 132/322 |
| 4,605,025 | 8/1986 | McSpadden ........................... 132/322 |
| 4,830,032 | 5/1989 | Jousson . |
| 4,880,382 | 11/1989 | Moret . |
| 5,016,660 | 5/1991 | Boggs . |
| 5,020,554 | 6/1991 | Feinberg . |
| 5,033,150 | 7/1991 | Gross et al. ........................... 132/322 |
| 5,069,233 | 12/1991 | Ritter . |
| 5,085,236 | 2/1992 | Odneal et al. . |
| 5,170,809 | 12/1992 | Imai et al. ............................. 132/383 |
| 5,411,041 | 5/1995 | Ritler ................................... 132/322 |

*Primary Examiner*—Paul J. Hirsch
*Attorney, Agent, or Firm*—Thomas I. Rozsa; Tony D. Chen

[57] ABSTRACT

An electrically driven dental flossing device which is used for flossing teeth. A flossing assembly is adapted to be mounted to the electrically driven dental flossing device. The dental flossing assembly includes a disposable floss holder which comprises a bow with a stem which in turn is replaceably mounted to a unitary driving shaft adaptor which in turn is mounted to the upper end of the electrically driven dental flossing device. The dental flossing device is gripped in the hand and the thumb is placed over the normally open spring urged thumb switch means. The flossing device works such that the dental floss material on the floss bow moves reciprocally between the teeth when the switch means is activated to energize a motor means within the handle to operate a gearing means which in turn moves the driving shaft adaptor in a reciprocating straight line in a back and forth motion to move the floss bow relative to the interproximal surfaces of the teeth.

14 Claims, 2 Drawing Sheets

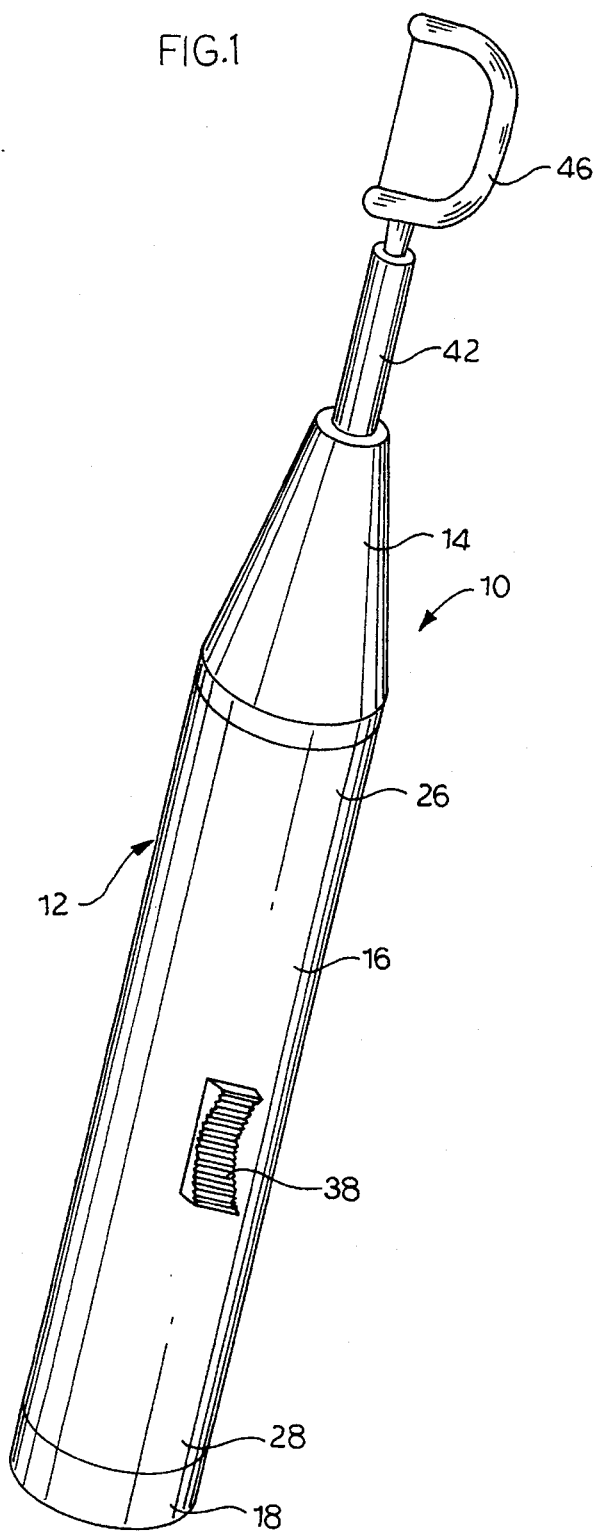
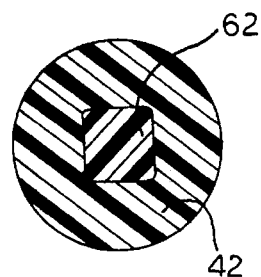

AUTOMATIC DENTAL FLOSSING DEVICE

BACKGROUND OF THE INVENTION

1. Field of the Invention

The present invention relates to the field of dental flossing devices. More particularly, the present invention relates to the field of electrically driven dental flossing devices.

2. Description of the Prior Art

It is common knowledge that flossing teeth is a very important part of home dental hygiene. However, flossing is widely ignored by many or most individuals. Many people are uncertain as to the correct method. In general, dental floss is usually supplied in a spool. To use it, a short length of floss is cut from the spool, wrapped around fingers of opposite hands, and inserted into the mouth and between the teeth. The maneuvering of the floss between the teeth with the fingers is very awkward for many people.

In the prior art, certain dental flossing devices for holding floss for use between the teeth are known. However, the prior art devices have not been entirely adequate. Specifically, they are cumbersome and bulky and are difficult to use.

The following eight (8) prior art patents were uncovered in the pertinent field of the present invention:

1. U.S. Pat. No. 4,235,253 issued to Moore on Nov. 25, 1980 for "Electric Dental Flosser" (hereafter "the Moore patent");
2. U.S. Pat. No. 4,245,658 issued to Lecouturier on Jan. 20, 1981 for "Automatic Flossing Apparatus" (hereafter "the Lecouturier patent");
3. U.S. Pat. No. 4,830,032 issued to Jousson on May 16, 1989 for "Power Driven Flossing Device" (hereafter "the Jousson patent");
4. U.S. Pat. No. 4,880,382 issued to Moret et al. on Nov. 14, 1989 for "Integrated Oral Hygiene System" (hereafter "the Moret patent");
5. U.S. Pat. No. 5,016,660 issued to Boggs on May 21, 1991 for "Automatic Flossing Tool" (hereafter "the Boggs patent");
6. U.S. Pat. No. 5,020,554 issued to Feinberg on Jun. 4, 1991 for "Dental Floss Dispenser and Applicator" (hereafter "the Feinberg patent");
7. U.S. Pat. No. 5,069,233 issued to Ritter on Dec. 3, 1991 for "Method and Apparatus for Removing Debris from Between and Around Teeth" (hereafter "the Ritter patent"); and
8. U.S. Pat. No. 5,085,236 issued to Odneal et al. on Feb. 4, 1992 for "Dental Floss Machine" (hereafter "the Odneal patent").

The Moore patent discloses an electrically driven dental floss device which has a tip with a forked end adapted to hold a short piece of dental floss tautly across the forked end. The tip is secured to an output shaft on a handle. The device is designed such that the dental floss moves between the teeth. A switch is depressed to energize a motor within the handle to move the tip in a reciprocating straight line up and down to move the floss upwardly and downwardly relative to the surface of the tooth.

The Lecouturier patent discloses an automatic flossing apparatus. The apparatus stores dental floss, holds it automatically under tension and agitates and renews the floss during its manipulations. The floss unwinds from one spool and rolls onto another automatically. The floss makes a complete circuit passing by an oscillator imparting back and forth movements to the floss and subsequently to a two-pronged headpiece holding the floss under tension across the two prongs. The spools are connected by a clutch and crank transmission mechanism.

The Jousson patent discloses a power driven flossing device. It includes a dental floss holder which has a pair of downwardly curved tines, one of the tines being smaller than the other. The proximal end of each tine has a rounded surface around which the dental floss is wound for use. The longer tine is bent at a much greater angle than the smaller tine. The lower end of the floss base is friction fitted on the end of the shaft. A rotational oscillating motion is imparted to the floss holder.

The Moret patent discloses an integral oral hygiene system which includes an electric toothbrush. The toothbrush can be replaced by an interproximal gum stimulator, an interproximal brush or a floss holder.

The Boggs patent discloses an automatic flossing tool. It includes a hollow handle portion with a bifurcated head portion mounted on the upper end of the handle. A pair of parallel arms extend at an angle to the axis of the handle and are formed with slots which are on the facing sides of each of the arms. Within each of the arms are a pair of tines which are capable of reciprocal movement within the respective arms by means of a crank which is driven through suitable gearing by a motor. A pair of drive wheels are mounted adjacent the other ends of each of the tines and a loop of dental flossing material is positioned about the drive wheels.

The Feinberg patent discloses a dental floss dispenser and applicator. It has a hollow handle for holding a supply of dental floss and a pair of intermeshing gear wheels mounted within the handle for advancing the dental floss through a pathway. The Pathway contains a dental floss anchoring member, a pair of prongs for holding a section of dental floss in position for use and a pair of intermeshing gears in the handle for pulling the dental floss through the pathway.

The Ritter patent discloses an automatic dental flosser. It includes a housing with a handle and an operating head. The operating head includes a pair of hollow tines which extend in a first plane. A flossing assembly is operable from between and around the teeth. The flossing assembly includes a support member for supporting the flossing material. A first portion of the support member is disposed in the hollow tines while a second portion of the support member is removed therefrom. A drive member is operably associated with the first portion of the flossing assembly for linerably displacing the support member.

The Odneal patent discloses a dental floss machine. It includes a dental flossing attachment which imparts an oscillatory motion to a strand of dental floss. The attachment is mounted on a drive shaft of an electric tooth brush. The attachment has a housing which contains a supply spool and a take-up spool. An advancing mechanism is provided whereby fresh floss is positioned between the two prongs at the end of the housing by turning a knob without the need for manual threading of the dental floss through grooves.

In general, all of the above prior art devices are cumbersome for providing interdental cleaning and also are not efficient for changing floss for use by more than one person. Therefore, it is highly desirable to have a very efficient and also very effective design and construction of an electrically driven dental flossing device. It is also desirable to provide a device with the capability of rapidly and effortless changing the floss bow.

SUMMARY OF THE INVENTION

The present invention is an electrically driven dental flossing device for flossing teeth of a user. The present invention includes a dental flossing assembly adapted to be mounted to the electrically driven dental flossing device. The dental flossing assembly includes a disposable floss holder which comprises a bow with a stem which in turn is replaceably mounted to a unitary driving shaft adaptor which in turn is mounted to the upper end of the electrically driven dental flossing device. The dental flossing device is gripped in the hand and the thumb is placed over the normally open spring urged thumb switch means. The flossing device works such that the dental floss material on the floss bow moves reciprocally between the teeth when the switch means is activated to energize a motor means within the handle to operate a gearing means which in turn moves the driving shaft adaptor in a reciprocating straight line in a back and forth motion to move the floss bow relative to the interproximal surfaces of the teeth. The dental flossing device is battery operated, e.g. two alkaline 'AA' batteries or two rechargeable batteries; however, the device can also be electrically operated by A/C current.

The length of the stroke is limited to approximately two (2) millimeters, thus preventing any harmful damage to the gingiva.

It is therefore an object of the present invention to provide an electrically driven dental flossing device which can move the dental floss bow in a back and forth motion between two teeth to properly clean and remove food particles from behind and between the teeth, where the motion of the dental floss will not damage the gingival tissue.

It is also an object of the present invention to provide a disposable dental floss bow which has a dental floss material thereon and capable of being removably mounted to an electrically driven dental flossing device, so that once the dental floss bow is used by an individual, the used dental floss bow is replaced by a new disposable dental floss bow for providing for subsequent use by the same person or other users.

It is an additional object of the present invention to provide a unitary driving shaft adaptor which is adapted to an electrically driven dental flossing device with a reciprocating motion. A disposable dental floss bow in turn is adapted to the driving shaft adaptor, so that the disposable dental floss bow can easily be replaced to provide for subsequent users.

It is a further object of the present invention to provide an electrically driven dental flossing device which is capable of being used by arthritic or elderly people having problems with their hands.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated:

FIG. 1 is a perspective view of the preferred embodiment of the present invention electrically driven dental flossing device;

FIG. 4 is an enlarged cross-sectional view taken along line 4—4 of FIG. 2.

DESCRIPTION OF THE PREFERRED EMBODIMENT

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Figure 2:
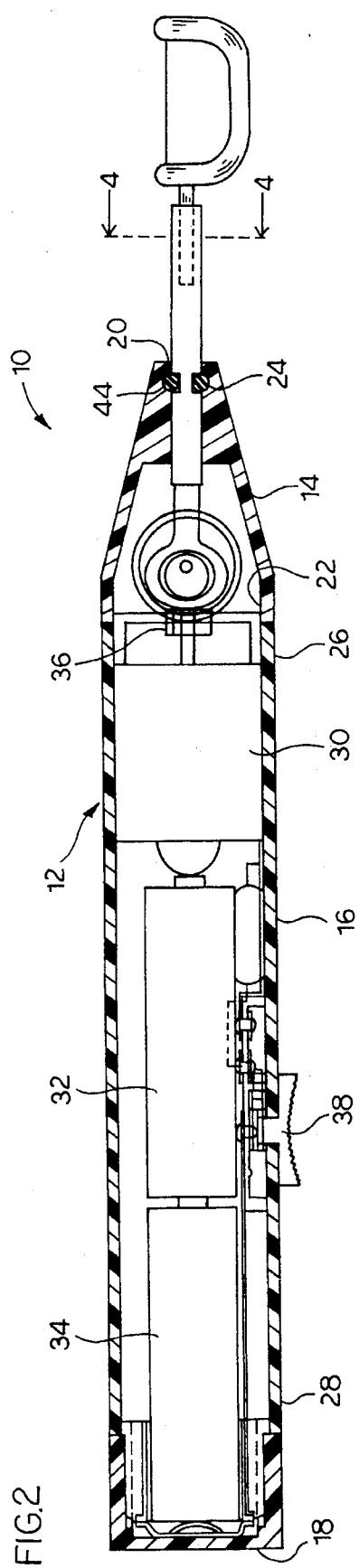
FIG. 2 is a partial cross-sectional view of the dental flossing device.

FIG. 1 shows a perspective view of the present invention electrically driven dental flossing device 10 for removing debris from between and around teeth of an individual. FIG. 2 shows a partial cross-sectional view of the electrically driven dental flossing device 10. Referring to FIGS. 1 and 2, the dental flossing device 10 includes a generally elongated hollow housing 12 which includes a handle portion 16, a hollow cone shaped nose portion 14 and a cap portion 18. The handle portion 16 has an upper end 26 and a lower end 28. The nose portion 14 has a narrow opening 20 at a narrow end which extends through to a wide opening 22 at the other end, and an inner annular recess 24 located adjacent to the narrow end.

The wide opening end 22 of the nose portion 14 is attached and secured onto the upper end 26 of the handle portion 16. The cap portion 18 is threadedly engaged and secured onto the lower end 28 of the handle portion 16. When the nose and cap portions 14 and 18 are attached to the handle portion 16, they form the housing 12 of the electrically driven dental flossing device 10. The housing 12 which supports the components of the present invention is structurally rigid. It may be inexpensively molded out of a thermoplastic material.

A motor means 30 is mounted within the handle portion 16 and located adjacent to the upper end 26. The motor means 30 is powered by a suitable power source such as two 1.5 volts alkaline 'AA' batteries 32 and 34 which are located within the handle portion 16 and are replaceable by removing the cap portion 18 from the handle portion 16. It should be understood that the two alkaline 'AA' batteries 32 and 34 may be two 'AA' rechargeable batteries. Other sources of power may include the standard AC current.

A gearing means 36 is mounted within the cone shaped nose portion 14 and coupled with the motor means 30 for reciprocating movement. A switch means 38 is mounted on a side of the handle portion 16 and is coupled to the motor means 30 and the two batteries 32 and 34 for activating the motor means 30. The two batteries 32 and 34 drive the motor means 30 which in turn operates the gearing means 36. As an example, the motor means 30 has a motor torque of ninety (90) grams per millimeter.

Figure 3:
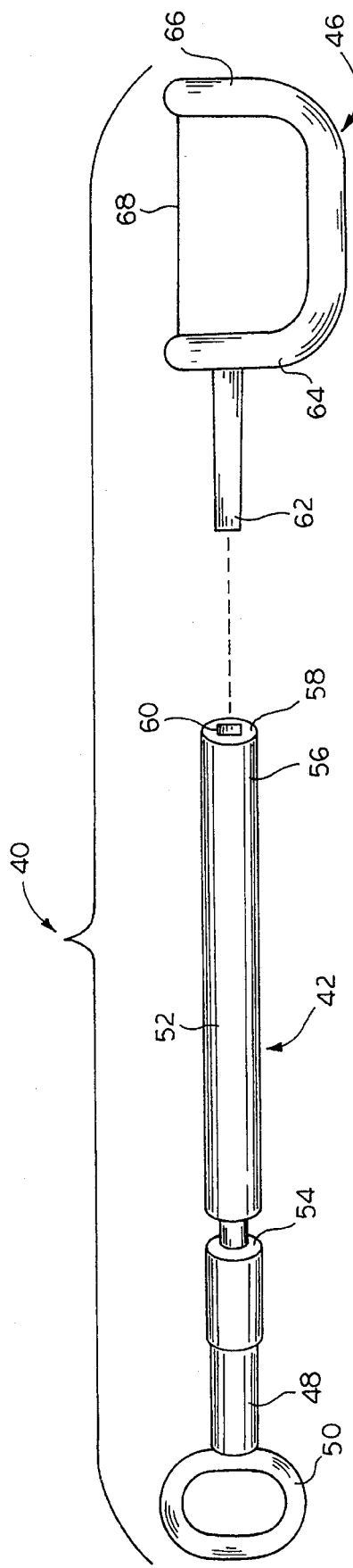
FIG. 3 is an enlarged exploded perspective view of a dental flossing assembly, showing a dental floss bow adapted to a driving shaft adaptor.

FIG. 3 shows an enlarged exploded view of a dental flossing assembly 40. FIG. 4 shows an enlarged cross sectional view of the dental flossing assembly 40. Referring to FIGS. 3 and 4, there is shown at 40 the dental flossing assembly which includes an elongated driving shaft adaptor 42 and a disposable dental floss bow 46. The driving shaft adaptor 42 has a proximal section 48 with a proximal end 50, a middle section 52 with an annular groove 54, and a distal section 56 with a distal end 58. The proximal end 50 is shaped like a non-circular ring and the distal end 58 has a square shaped opening 60. The driving shaft adaptor 42 is mounted within the cone shaped nose portion 14 such that the proximal end ring 50 is coupled to the gearing means 36 and the distal section 56 protrudes out from the narrow opening 20 of the cone shaped nose portion 14. A flexible O-ring 44 is installed within the inner annular recess 24 on the cone shaped nose portion 14 (shown in FIG. 2). The distal section 56 of the driving shaft adaptor 42 is inserted through the narrow opening 20 and away from the nose portion 14 so that the O-ring 44 is positioned within the annular groove 54 on the driving shaft adaptor 42. Once the O-ring 44 is in place, it will prevent the flow of water inside the housing 12. The O-ring 44 may be made from rubber material or any other suitable material, which will prevent water from infiltrating into the housing 12.

The disposable dental floss bow 46 has a C-shaped support which supports a pair of parallel spaced apart prongs or tines 64 and 66. An elongated stem or shaft 62 is integrally connected to the prong 64 such that the elongated stem is perpendicular to the prong 64. The pair of the prongs 64 and 66 are holding a dental floss material 68 therebetween in position for applying the dental floss material to the teeth of the user. The elongated stem 62 is generally a square shape body and can be press-fit into the square shaped opening 60 at the distal end 58 of the driving shaft adaptor 42.

To use the present invention device, the user simply places the disposable dental floss bow 46 into the driving shaft adaptor 42 and then within their mouth in a position such that the prong 66 of the dental floss bow 46 is located behind their teeth, while the other prong 64 of the dental floss bow 46 is located outside the teeth and guides the dental floss material 68 into the space between adjacent teeth. As this is done, the reciprocal movement of the driving shaft adaptor 42 will cause the movement of the dental floss material 68 to accomplish thorough and effective flossing of the user's teeth. The user can activate the dental flossing device 10 by activating the switch means 38 to the "ON" position. This causes the motor means 30 to operate the gearing means 36 to move the driving shaft adaptor 42 which in turn moves the disposable dental floss bow 46 in short back and forth motion. The motion of the driving shaft adaptor 42 is very small and preferably only about two (2) mm at the dental floss level.

Once the disposable dental floss bow 46 is used by an individual, the disposable dental floss bow 46 is disposed and can be replaced by a new disposable dental floss bow to provide sterile use for subsequent users. The unique feature of the present invention dental flossing device 10 is that the driving shaft adaptor 42 has a holding feature for retaining the disposable dental floss bow 46 in position.

The dental flossing device 10 can be made from several materials. A manufacturing process which could accommodate the construction of the dental flossing device 10 is an injection, thermoform, etc. or other molding process. By way of example, the dental flossing device 10 can be made of ABS plastic material.

Defined in detail, the present invention is a dental flossing device for removing debris from between and around a user's teeth, comprising: (a) a generally elongated hollow cylindrical housing having a handle portion with an upper end and a lower end, a cap portion removably attached to and covering said lower end of said hollow cylindrical housing, and a hollow cone shaped nose portion removably attached to said upper end of said hollow cylindrical housing, the nose portion having a wide end, a narrow end, a wide opening at the wide end extending to a narrow opening at the narrow end, and an inner annular recess located adjacent to the narrow end; (b) an elongated driving shaft adaptor having a distal section with a distal end, a middle section, and a proximal section with a proximal end, the distal end having a square shaped opening, the proximal end having a non-circular ring located within said hollow cone shaped nose portion such that the distal section of the driving shaft adaptor extends through said narrow opening of said cone shaped nose; (c) a disposable dental floss bow having a C-shaped support and an elongated stem integrally attached to the support, the C-shaped support having a pair of spaced apart parallel prongs for holding a dental floss material therebetween, the elongated stem press-fitted within said square shaped opening at said distal end of said driving shaft adaptor; (d) motor means mounted within said hollow cylindrical housing and adjacent to said upper end of said hollow cylindrical housing; (e) battery means placed coaxially inside said hollow cylindrical housing for providing electrical power to said motor means; (f) gearing means mounted within said hollow cone shaped nose portion and coupling said motor means and said non-circular ring at said proximal end of said diving shaft adaptor for reciprocating movement of said driving shaft adaptor, which in turn causes said disposable dental floss bow to move in short back and forth motion; (g) switch means mounted on said hollow cylindrical housing for activating said motor means; and (h) a flexible O-ring placed within said inner annular recess of said hollow cone shaped nose portion and aligned with and sealably between said annular groove of said driving shaft adaptor for preventing flow of water inside said hollow cylindrical housing; (i) whereby when said dental floss material of said dental floss bow is positioned between the teeth, the user can switch said switch means to energize said motor means, which causes said gearing means to move through said reciprocating movement of said driving shaft adaptor which in turn moves said floss material in a back and forth motion between the teeth to remove debris from between and around the teeth.

Defined broadly, the present invention is a dental flossing device for removing debris from between and around a user's teeth, comprising: (a) a hollow cylindrical housing having a handle portion with a first end and a second end, a cap portion removably attached to and covering said second end of said hollow cylindrical housing, and a hollow cone shaped nose portion removably attached to said first end of said hollow cylindrical housing, the nose portion having a first end, a second end, and a first opening at the first end extending to a second opening at the second end; (b) a driving shaft adaptor having a distal section with a distal end and a proximal section with a proximal end, the distal end having an opening, the proximal end located within said hollow cone shaped nose portion such that the distal section of the driving shaft adaptor extends through said second opening of said cone shaped nose portion; (c) a dental floss bow having a pair of parallel prongs for holding a dental floss material therebetween and an integral stem press-fitted within said opening at said distal end of said driving shaft adaptor; (d) motor means mounted within said hollow cylindrical housing and adjacent to said first end of said hollow cylindrical housing; (e) power source means placed coaxially inside said hollow cylindrical housing for providing electrical power to said motor means; (f) gearing means mounted within said hollow cone shaped nose portion and coupling said motor means and said proximal end of said diving shaft adaptor for reciprocating movement of said driving shaft adaptor, which in turn causes said dental floss bow to move in short back and forth motion; (g) switch means mounted on said hollow cylindrical housing for activating said motor means; and (h) a sealing means for preventing flow of water inside said hollow cylindrical housing; (i) whereby when said dental floss material of said dental floss bow is positioned between the teeth, the user can activate said switch means to energize said motor means, which causes said gearing means to move through said reciprocating movement of said driving shaft adaptor which in turn moves said floss material in a back and forth motion between the teeth to remove debris from between and around the teeth.

Defined more broadly, the present invention is a dental flossing device for removing debris from between and around a user's teeth, comprising: (a) a housing; (b) a nose attached to an open end of said housing and having an opening; (c) a driving shaft adaptor having a distal end and a proximal end and placed within said nose such that the distal end extends through said opening of said nose; (d) a floss bow having two prongs for holding a floss material therebetween and an integral stem detachably attachable to said distal end of said driving shaft adaptor; (e) motor means placed within said housing; (f) power source means placed within said housing for providing electrical power to said motor means; (g) gearing means placed within said housing for coupling said motor means and said proximal end of said diving shaft adaptor to cause reciprocating movement of said driving shaft adaptor, which in turn moves said floss bow in short back and forth motion; and (h) switch means for activating said motor means; (i) whereby when said floss material of said floss bow is positioned between the teeth, the user can activate said switch means to energize said motor means, which causes said gearing means to move through said reciprocating movement of said driving shaft adaptor which in turn moves said floss material in a back and forth motion between the teeth to remove debris from between and around the teeth.

Of course the present invention is not intended to be restricted to any particular form or arrangement, or any specific embodiment disclosed herein, or any specific use, since the same may be modified in various particulars or relations without departing from the spirit or scope of the claimed invention hereinabove shown and described of which the apparatus shown is intended only for illustration and for disclosure of an operative embodiment and not to show all of the various forms or modifications in which the present invention might be embodied or operated.

The present invention has been described in considerable detail in order to comply with the patent laws by providing full public disclosure of at least one of its forms. However, such detailed description is not intended in any way to limit the broad features or principles of the present invention, or the scope of patent monopoly to be granted.

What is claimed is:

1. A dental flossing device for removing debris from between and around a user's teeth, comprising:
   a. a generally elongated hollow cylindrical housing having a handle portion with an upper end and a lower end, a cap portion removably attached to and covering said lower end of said hollow cylindrical housing, and a hollow cone shaped nose portion removably attached to said upper end of said hollow cylindrical housing, the nose portion having a wide end, a narrow end, a wide opening at the wide end extending to a narrow opening at the narrow end, and an inner annular recess located adjacent to the narrow end;
   b. an elongated driving shaft adaptor having a distal section with a distal end, a middle section, and a proximal section with a proximal end, the distal end having a square shaped opening, the proximal end having a non-circular ring located within said hollow cone shaped nose portion such that the distal section of the driving shaft adaptor extends through said narrow opening of said cone shaped nose;
   c. a disposable dental floss bow having a C-shaped support and an elongated stem integrally attached to the support, the C-shaped support having a pair of spaced apart parallel prongs for holding a dental floss material therebetween, the elongated stem press-fitted within said square shaped opening at said distal end of said driving shaft adaptor;
   d. motor means mounted within said hollow cylindrical housing and adjacent to said upper end of said hollow cylindrical housing;
   e. battery means placed coaxially inside said hollow cylindrical housing for providing electrical power to said motor means;
   f. gearing means mounted within said hollow cone shaped nose portion and coupling said motor means and said non-circular ring at said proximal end of said driving shaft adaptor, where the gearing means moves said driving shaft adaptor in a reciprocating motion, which in turn causes said disposable dental floss bow to move in short back and forth motion;
   g. switch means mounted on said hollow cylindrical housing for activating said motor means; and
   h. a flexible O-ring placed within said inner annular recess of said hollow cone shaped nose portion and aligned with and sealably between said annular groove of said driving shaft adaptor for preventing flow of water inside said hollow cylindrical housing;
   i. whereby when said dental floss material of said dental floss bow is positioned between the teeth, the user can activate said switch means to energize said motor means, which causes said gearing means to move through said reciprocating motion of said driving shaft adaptor which in turn moves said floss material in said back and forth motion between the teeth to remove debris from between and around the teeth.

2. The dental flossing device in accordance with claim 1 wherein said housing, said nose and cap portions and said driving shaft adaptor are made of ABS plastic material.

3. The dental flossing device in accordance with claim 1 wherein said battery means are two alkaline 'AA' batteries.

4. A dental flossing device for removing debris from between and around a user's teeth, comprising:
   a. a hollow cylindrical housing having a handle portion with a first end and a second end, a cap portion removably attached to and covering said second end of said hollow cylindrical housing, and a hollow cone shaped nose portion removably attached to said first end of said hollow cylindrical housing, the nose portion having a first end, a second end, and a first opening at the first end extending to a second opening at the second end;
   b. a driving shaft adaptor having a distal section with a distal end and a proximal section with a proximal end, the distal end having an opening, the proximal end located within said hollow cone shaped nose portion such that the distal section of the driving shaft adaptor extends through said second opening of said cone shaped nose portion;
   c. a dental floss bow having a pair of parallel prongs for holding a dental floss material therebetween and an integral stem press-fitted within said opening at said distal end of said driving shaft adaptor;

d. motor means mounted within said hollow cylindrical housing and adjacent to said first end of said hollow cylindrical housing;

e. power source means placed coaxially inside said hollow cylindrical housing for providing electrical power to said motor means;

f. gearing means mounted within said hollow cone shaped nose portion and coupling said motor means and said proximal end of said driving shaft adaptor, where the gearing means moves said driving shaft adaptor in a reciprocating motion, which in turn causes said dental floss bow to move in short back and forth motion;

g. switch means mounted on said hollow cylindrical housing for activating said motor means; and h. a sealing means for preventing flow of water inside said hollow cylindrical housing;

i. whereby when said dental floss material of said dental floss bow is positioned between the teeth, the user can activate said switch means to energize said motor means, which causes said gearing means to move through said reciprocating motion of said driving shaft adaptor which in turn moves said floss material in said back and forth motion between the teeth to remove debris from between and around the teeth.

5. The dental flossing device in accordance with claim 4 wherein said housing, said nose and cap portions and said driving shaft adaptor are made of ABS plastic material.

6. The dental flossing device in accordance with claim 4 wherein said power source means includes at least two 1.5 volts batteries.

7. The dental flossing device in accordance with claim 4 wherein said sealing means is a flexible O-ring.

8. The dental flossing device in accordance with claim 4 wherein said dental floss bow is disposable.

9. A dental flossing device for removing debris from between and around a user's teeth, comprising:

a. a housing;

b. a nose attached to an open end of said housing and having an opening;

c. a driving shaft adaptor having a distal end and a proximal end and placed within said nose such that the distal end extends through said opening of said nose;

d. a floss bow having two prongs for holding a floss material therebetween and an integral stem detachably attachable to said distal end of said driving shaft adaptor;

e. motor means placed within said housing;

f. power source means placed within said housing for providing electrical power to said motor means;

g. gearing means placed within said housing and coupled to said motor means and said proximal end of said driving shaft adaptor, where the gearing means moves said driving shaft adaptor in a reciprocating motion, which in turn moves said floss bow in a back and forth motion; and h. switch means for activating said motor means;

i. whereby when said floss material of said floss bow is positioned between the teeth, the user can activate said switch means to energize said motor means, which causes said gearing means to move through said reciprocating motion of said driving shaft adaptor which in turn moves said floss material in said back and forth motion between the teeth to remove debris from between and around the teeth.

10. The dental flossing device in accordance with claim 9 wherein said housing, said nose and said driving shaft adaptor are made of plastic material.

11. The dental flossing device in accordance with claim 9 wherein said power source means includes at least two 1.5 volts batteries.

12. The dental flossing device in accordance with claim 9 wherein said floss bow is disposable.

13. The dental flossing device in accordance with claim 9 further comprising a sealing means for preventing flow of water inside said housing.

14. The dental flossing device in accordance with claim 13 wherein said sealing means comprises a flexible O-ring.

* * * * *